United States Patent [19]

York

[11] Patent Number: 4,996,993
[45] Date of Patent: Mar. 5, 1991

[54] IN VIVO OSMOMETER

[76] Inventor: Kenneth K. York, 2300 N. Edgemont, Los Angeles, Calif. 90027

[21] Appl. No.: 280,984

[22] Filed: Dec. 7, 1988

[51] Int. Cl.$^5$ ............................. A61B 5/03; A61B 5/05
[52] U.S. Cl. ..................................... 128/734; 128/748; 73/753; 324/692
[58] Field of Search ................... 128/734, 748; 73/753; 324/65 P

[56] References Cited

U.S. PATENT DOCUMENTS 2,763,935  9/1956  Whaley et al. .................... 324/65 P
4,297,890  11/1981 Hok ...................................... 73/753
4,449,396  5/1984  Bzdula ............................ 324/65 P X

FOREIGN PATENT DOCUMENTS 1321405  7/1987  U.S.S.R. ............................... 128/734

OTHER PUBLICATIONS

Ulmsten et al., "A new transducer ... recordings". J. Met, vol. 3, No. 6, Nov. 1979, pp. 295-298.
Brochure re the Wescor 5500 Vapor Pressure Osmometer.
Brochure re the Wescor 3100 Sweat-Chek Sweat Conductivity Analyzer.
"Electrical Conductivity of Sweat," by Schwachman et al., Pediatrics, Jul. 1963, pp. 85-87.
"The Total Osmotic Pressure of Tears in Normal and Various Pathological Conditions," by Mastman et al., Archives of Ophthalmology, vol. 65, Apr. 1961, pp. 510-513.
"Osmolarity of Tear Microvolumes in Kiratoconjunctivititis sicca," by Gilbard et al., from Arch Ophthalmol, vol. 96, Apr. 1978, pp. 677-681.

Primary Examiner—Lee S. Cohen

[57] ABSTRACT

A first exemplary embodiment of an osmometer for the in vivo measurement of the osmolarity of a bodily fluid such as tears or sweat comprises a detachable, preferably disposable, probe in combination with means for measuring the conductivity between two electrodes of the probe. The osmometer further comprises means for converting the measured value of conductivity of the in vivo sample into a corresponding value of osmolarity and display means for displaying a visible representation of that value.

In a second exemplary embodiment a sensor of some physical quantity (such as dew point temperature) related to the vapor pressure from a bodily fluid is mounted inside a confining, generally concave shell which is placed adjacent to a portion of the human body for a measurement to be made. For the case of measuring tear osmolarity in the open eye, the confining shell could take the form of a conventional eyecup. The sensor can be a thermocouple or thermistor controlled by a microprocessor to measure vapor pressure by the dew point depression method.

18 Claims, 3 Drawing Sheets

IN VIVO OSMOMETER

BACKGROUND OF THE INVENTION

1. Field of the Invention

The invention relates generally to the field of devices for measuring the osmotic pressure of human body fluids, and in particular to apparatus for measuring, in vivo, the osmolarity of tears.

2. Description of the Related Art

An osmometer is a device for measuring osmotic pressure. The osmotic pressure of a solution is defined as the excess pressure that must be applied to the solution to prevent the passage into it of solvent that is separated from the solution by a semipermeable membrane which allows only solvent molecules to pass through. The osmolarity of a solution is a characteristic determined by the ionic concentration of a dissolved substance per unit quantity of solvent.

The importance of the osmotic pressure of various body fluids relates to correlations that have been sometimes noted between the osmolarity of a particular fluid and some pathological condition of the body. For example, the relationship of the osmotic pressure of tears to various pathologic conditions is discussed in the article "The Total Osmotic Pressure of Tears in Normal and Various Pathologic Conditions," by Gary J. Mastman et al., in ARCHIVES OF OPHTHALMOLOGY, Vol. 65, Apr., 1961, pages 71/509-75/513.

The particular pathologic condition designated "dry eye" and its connection to tear film osmolarity is described in the article "Osmolarity of Tear Microvolumes in Keratoconjunctivitis Sicca," by Jeffrey P. Gilbard et al., in Arch. Ophthalmol., Vol. 96, Apr., 1978, pages 677-681. When the surface of the eye starts to dry out the tear film becomes hypertonic (elevated osmolarity), causing discomfort and epithelial damage.

Presently measurements are conventionally made in vitro by removing a tear sample from the eye using a micropipette and measuring the depression of the freezing point that results from heightened osmolarity. This technique is difficult to carry out and the results are plagued by many sources of error. It would be a great advance in the art of ophthalmological diagnostic testing if it were possible to measure, in vivo, the osmolarity of tears easily and accurately.

The osmolarity of sweat has been linked to cystic fibrosis. Measurements of the electrical conductivity of sweat in vitro have been used in the diagnosis of this condition in children. Information about this topic can be found in the article "Electrical Conductivity of Sweat—A Simple Diagnostic Test in Children," by H. Shwachman et al., in the journal PEDIATRICS, July 1963, pages 85-88. A sweat conductivity analyzer for in vitro measurements is produced commercially under the trademark Sweat.Chek by Wescor, Inc., 459 South Main Street, Logan, Utah 84231. It would be an important development in the art of medical diagnostic testing if it were possible to measure, in vivo, the osmolarity of sweat easily and accurately.

SUMMARY OF THE INVENTION

A first exemplary embodiment of an osmometer for the in vivo measurement of the osmolarity of a bodily fluid such as tears or sweat comprises a probe, preferably detachable and disposable, in combination with means for measuring the conductivity between two electrodes of the probe. The tips of the electrodes are either separated by an air gap, or the electrode tips are linked by a fine strip of absorbent material that is nonconducting until wet with body fluids. In either case the tips of the electrodes make contact with the bodily fluid to complete the conductivity measurement circuit. The osmometer further comprises means for converting the measured value of conductivity of the in vivo sample into a corresponding value of osmolarity and display means for displaying a visible representation of that value.

In a second exemplary embodiment a sensor of some physical quantity (such as dew point temperature) related to the vapor pressure from a bodily fluid is mounted inside a confining, generally concave shell which is placed adjacent to a portion of the human body for a measurement to be made. For the case of measuring tear osmolarity in the open eye, the confining shell could take the form of a conventional eyecup.

In one possible arrangement of the second exemplary embodiment the sensor comprises a thermocouple connected to a microprocessor controller which controls the temperature of the thermocouple and automatically directs a sequence of measurements of the sensor output to determine the vapor pressure and the corresponding value of osmolarity.

When the eyecup or occluder is placed over the eye, temperature and vapor pressure equilibrate in a short time inside the confined volume of vapor. The thermocouple senses the temperature of the air above the tear film in the open eye. The microprocessor sets a first measured value as a null or reference point value. Then, the thermocouple is Peltier-cooled below the dew point temperature by passing a current through it. Water begins to condense on its surface, forming tiny droplets. Next, the microprocessor allows the thermocouple temperature to be controlled exclusively by the water condensation taking place on it. The heat released by the condensing water causes a rise in thermocouple temperature, and a final, stable value is reached at that temperature for which condensation ceases (the dew point temperature). A conversion means converts the measured value to a corresponding value of osmolarity). A display means is provided for displaying a visible representation of the final osmolarity value.

A variation of the second exemplary embodiment employs a thermistor as the sensor with a separate Peltier cooling element in thermal contact with the thermistor and controlled by the controller. In the determination of vapor pressure by the dew point depression method described above the thermistor is cooled by passing a current through the Peltier element.

BRIEF DESCRIPTION OF THE DRAWINGS

The various features and advantages of the present invention will become apparent in light of the following detailed description taken together with the accompanying drawings, in which:

FIG. 2 is a side elevational view of one possible embodiment of the disposable tip portion of the osmometer;

DESCRIPTION OF THE PREFERRED EMBODIMENTS

Figure 1:
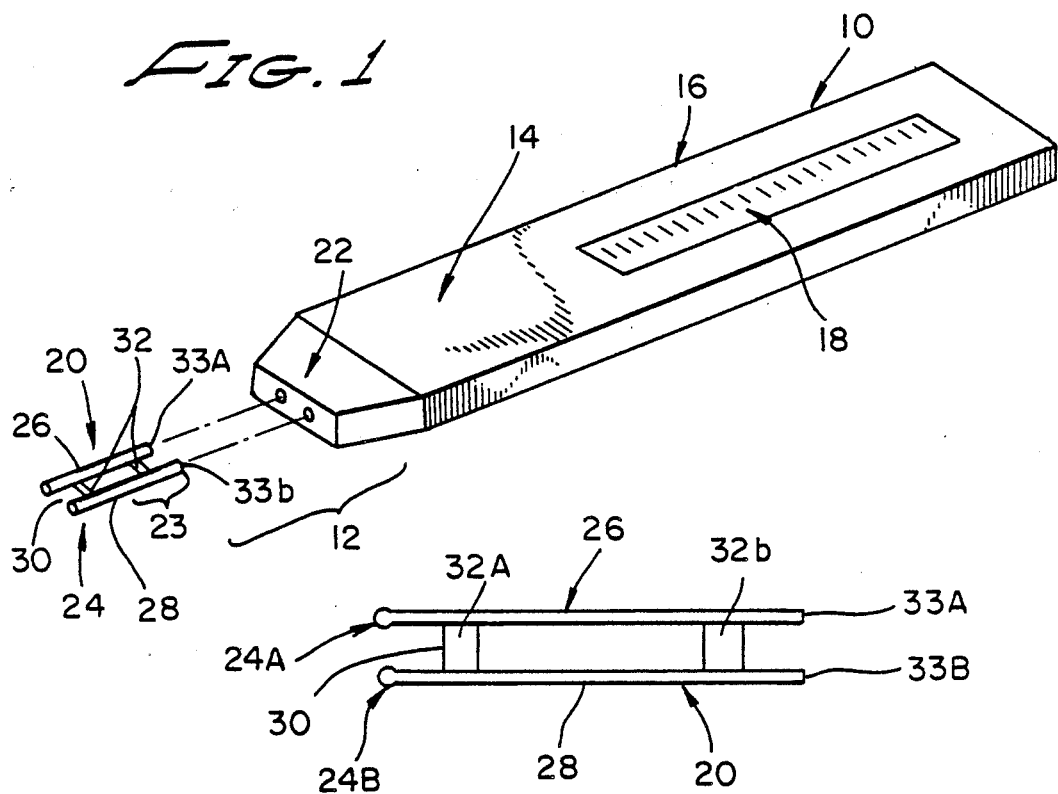
FIG. 1 is perspective view of a first exemplary embodiment of the in vivo osmometer of the present invention.

The apparatus of the present invention will be described in relation to FIGS. 1 through 8, with like reference numerals referring to like parts of the system.

Referring to FIG. 1, a perspective view of a first exemplary embodiment of the in vivo osmometer 10 of the present invention may be seen. Osmometer 10 comprises probe means 12 for defining an in vivo sample of a bodily fluid, and conductivity measuring means 14 connected to said probe means 12 for measuring the conductivity of the sample. Conductivity measuring means 14 comprises conversion means 16 (internal, not shown) for converting a measured value of conductivity to a corresponding value of osmolarity, and display means 18 for displaying a visible representation of the corresponding value of osmolarity.

Referring still to FIG. 1, probe means 12 comprises a replaceable tip portion 20 which can be coupled to conductivity measuring means 14 via connection means 22. Connection means 22 provides both mechanical and electrical connections between a proximal end 23 of tip portion 20 and conductivity measuring means 14. Distal end 24 of tip portion 20 has separated first and second electrically conductive electrodes 26 and 28 with a nonconductive gap 30 between them. Electrodes 26 and 28 are kept apart by separation means 32, which can be simple spacing elements as shown.

Connection means 22 can be mating holes which receive the proximal ends 33A and 33B of first and second electrodes 26 and 28 in some sort of snap-in arrangement, for example, so that tip portion 20 is easily and conveniently replaceable. Tip portion 20 may also be made to be disposable to obviate problems of sterilization between uses.

FIG. 2 is a side elevational view of one possible embodiment of the disposable tip portion 20 of the osmometer 10. Insulated first and second conducting electrodes 26 and 28 are held apart by insulating spacers 32A and 32B near either end of tip portion 20. The distal ends 24A and 24B of electrodes 26 and 28, respectively, end in blunt shapes suitable for touching delicate parts of the body such as the cornea. Each of the first and second electrode distal ends 24A and 24B would have a surface comprising a suitable material for contact with the body, such as gold or platinum. Between the blunt ends 24A and 24B of tip portion 20 is a nonconducting air gap 30. Proximal ends 33A and 33B of electrodes 26 and 28, respectively, have shapes which connect with matingly shaped parts of conductivity measuring means 14.

Figure 3:
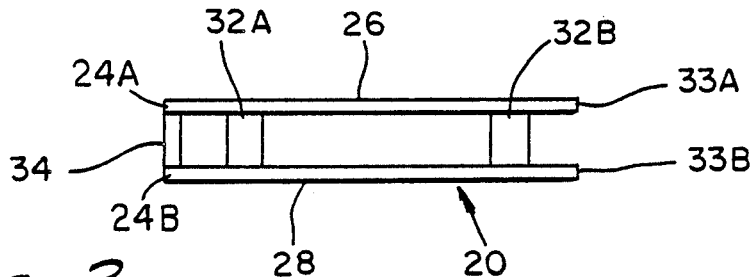
FIG. 3 is a side elevational view of a second possible embodiment of the disposable tip portion of the osmometer.

FIG. 3 is a side elevational view of a second possible embodiment of the disposable tip portion 20 of the osmometer 10. In this embodiment the gap between the distal ends 24A and 24B of electrodes 26 and 28 is bridged by a strip 34 of absorbent material. Strip 34 would be electrically nonconductive in the dry state, but would conduct when wetted with a small volume of bodily fluid. Various appropriate types of absorbent materials for strip 34 would include blotting or filter papers and threads of natural or synthetic material.

Figure 4:
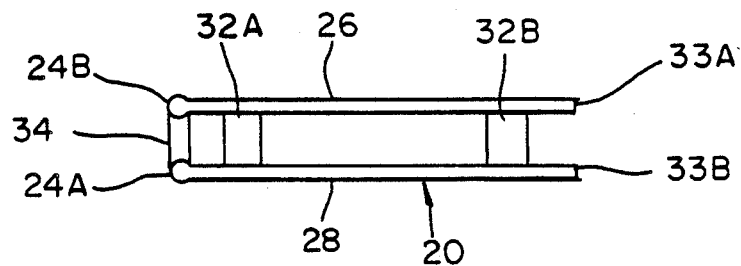
FIG. 4 is a side elevational view of a third possible embodiment of the disposable tip portion of the osmometer.

FIG. 4 is a side elevational view of a third possible embodiment of the disposable tip portion 20. This embodiment is in a sense a combination of the first two embodiments, since it includes blunt distal ends 24A and 24B of electrodes 26 and 28 bridged by a strip 34 of absorbent material. The conductivity measured while the blunt ends 24A and 24B are held against some part of the body would be partly due to conduction through the fluid on the body and partly due to conduction through the fluid absorbed by strip 34.

Figure 5:
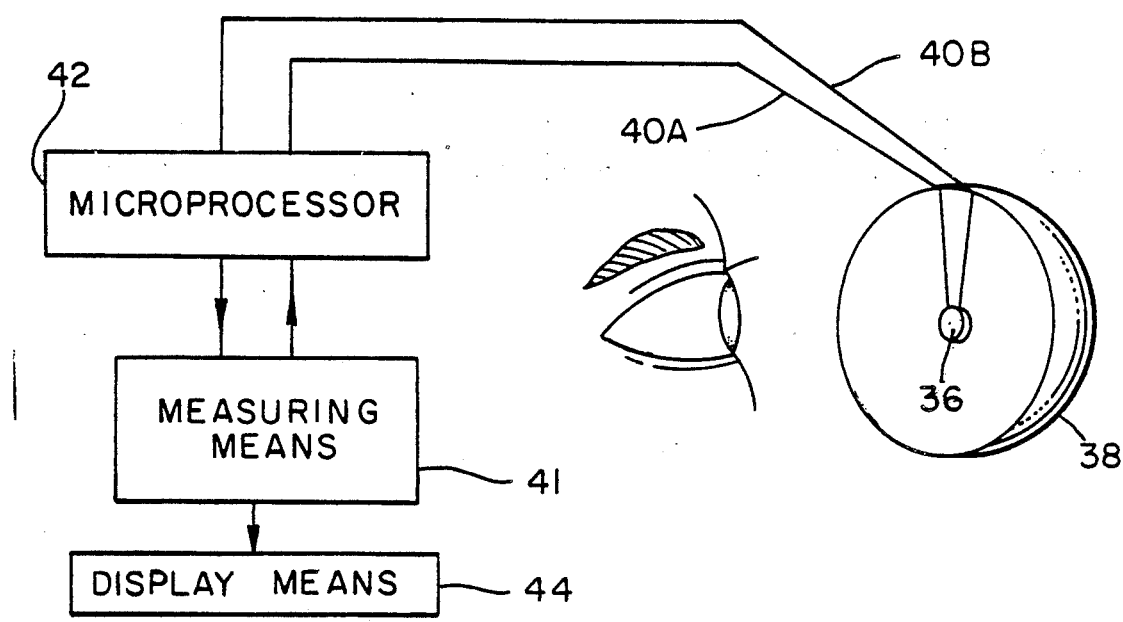
FIG. 5 is a perspective view of a second exemplary embodiment of the in vivo osmometer of the present invention.

Referring to FIG. 5, which is a perspective view, a second exemplary embodiment of the in vivo osmometer of the present invention may be seen. In this embodiment a sensor means 36 for sensing in vivo a physical quantity related to the vapor pressure of a bodily fluid is mounted inside vapor confinement means 38 for defining a closed volume containing the vapor of the bodily fluid. FIG. 5 shows an implementation of the invention for noninvasively determining the vapor pressure of the tear film in the open eye. A thermocouple junction serves as sensor means 36, connected by electrical leads 40A and 40B to a microprocessor controller 42, which in turn is connected with a measuring means 41 for measuring the temperature sensed by thermocouple junction 36. Microprocessor 42 controls the temperature of thermocouple junction 36 and programs a series of measurements made by it.

The thermocouple senses the temperature of the air above the tear film in the open eye when an eyecup or occluder serves as vapor confinement means 38. The eyecup or occluder serving as vapor confinement means 38 is shaped to fit snugly over the eye and eyelids and can comprise a clear, nonporous plastic material, for example. When the eyecup or occluder is placed over the eye, temperature and vapor pressure equilibrate in a short time inside the confined volume of vapor.

Microprocessor 42 sets a first measured value as a null or reference point value. Then, the thermocouple is Peltier-cooled below the dew point temperature. Water begins to condense on its surface, forming tiny droplets. Next, microprocessor 42 allows the thermocouple temperature to be controlled exclusively by the water condensation taking place on it. The heat released by the condensing water causes a rise in thermocouple temperature, and a final, stable value is reached at that temperature for which condensation ceases.

A display means 44 for displaying a visible representation of the final measured temperature is connected to microprocessor 42. Since dew point temperature is a function of vapor pressure and vapor pressure is in turn related to osmolarity, the osmometer 10 can be calibrated to display results directly in units of osmolarity.

Figure 6:
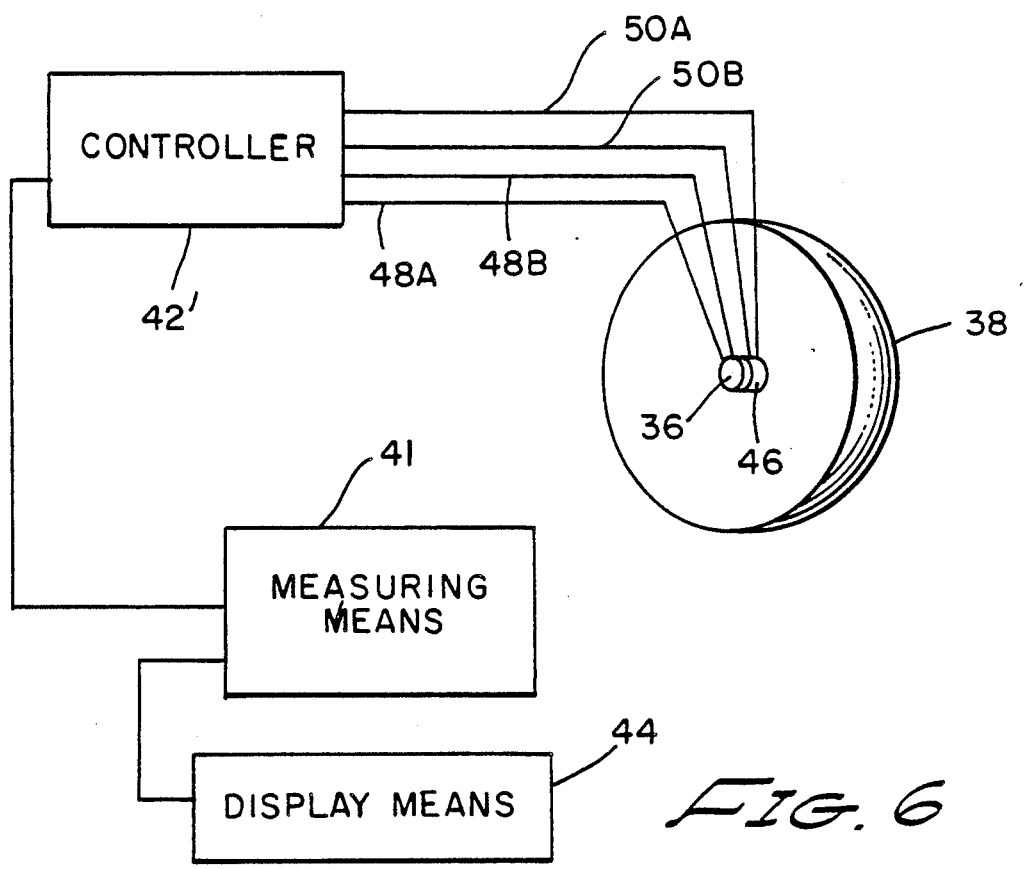
FIG. 6 is a perspective view of a variation of the second exemplary embodiment of the in vivo osmometer of the present invention, employing a thermistor and a Peltier cooling element.

FIG. 6 is a perspective view of a variation of the second exemplary embodiment of the in vivo osmometer of the present invention. In this variation, a thermistor 36' is the sensor and a Peltier cooling element 46 is mounted in thermal contact with thermistor 36'. Electrical leads 48A and 48B and 50A and 50B from thermistor 36' and Peltier cooling element 46 are connected to controller 42'. With this alternative arrangement, the vapor pressure can again be measured in the same way as described above, by the dew point depression method. Thermistor 36' is used to measure a reference temperature, controller 42' causes a current to be passed through Peltier element 46 so as to reduce the temperature of thermistor 36', and then the heat of condensation of vapor condensing on the surface of thermistor 36' results in a final equilibrium value of the temperature directly related to the osmolarity.

Figure 7:
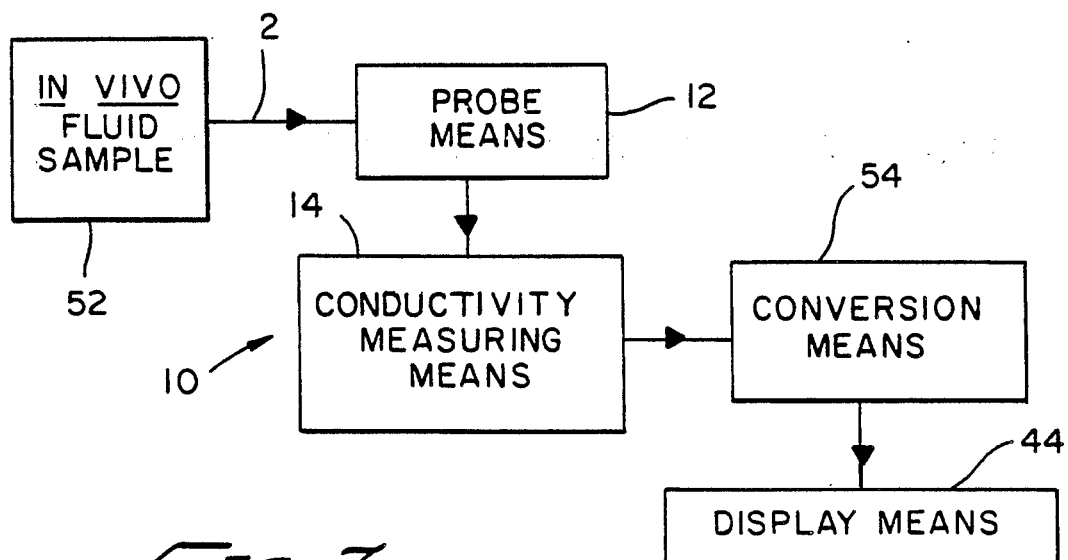
FIG. 7 is a schematic block diagram indicating the relationship of various components of the first exemplary embodiment of the invention.

FIG. 7 is a schematic block diagram indicating the relationship of various components of the first exemplary embodiment of the invention. Probe means 12 is placed in contact with a part of the body to define an in vivo fluid sample 52 of which conductivity measuring means 14 measures the conductivity. Conversion means 54 converts the measured value of conductivity to a corresponding value of osmolarity which is displayed by display means 44. Conversion means 54 could be a suitably calibrated scale printed on an analog output display, or, in the case of a digital output display, circuitry that converts a measured current through probe means 12 to a suitable electrical signal for display means 44. Suitable digital display types would include liquid crystal and light emitting diode displays.

Figure 8:
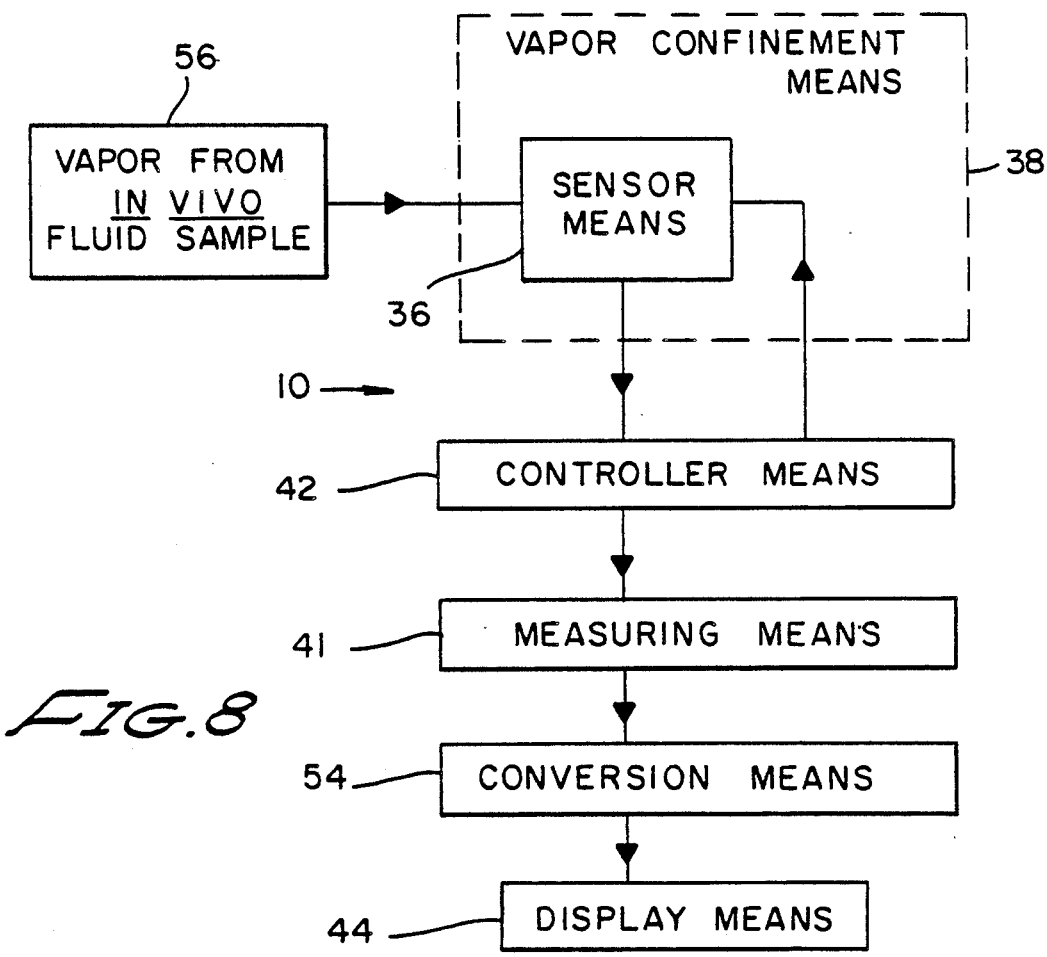
FIG. 8 is a schematic block diagram indicating the relationship of various components of the second exemplary embodiment of the invention.

FIG. 8 is a schematic block diagram indicating the relationship of various components of the second exemplary embodiment of the invention. Sensor means 36 inside vapor confinement means 38 senses a physical quantity (such as dew point temperature) which can be related to the vapor pressure of the vapor 56 from an in vivo fluid sample over which vapor confinement means 38 has been placed. Sensor means 36 is connected to measuring means 41 and to microprocessor controller 42, which controls the temperature of sensor means 36 and automatically directs the sequence of measurements taken to determine the vapor pressure via the dew point depression method. Conversion means 54 converts the measured value of the physical quantity related to vapor pressure to a corresponding value of osmolarity which is displayed by display means 44. Conversion means 54 could be a suitably calibrated scale printed on an analog output display, or, in the case of a digital output display, circuitry that converts a measured output from sensor means 36 to a suitable electrical signal for display means 44.

The above-described embodiments are furnished as illustrative of the principles of the invention, and are not intended to define the only embodiments possible in accordance with out teaching. Rather, the invention is to be considered as encompassing not only the specific embodiments shown, but also any others falling within the scope of the following claims.

What is claimed is:

1. An osmometer adapted for contact with the human eye comprising:
   probe means for contacting an in vivo sample of a bodily fluid on the human eye to make a conductivity measurement thereon;
   conductivity measuring means operatively connected to said probe means for measuring the conductivity of said sample;
   conversion means for converting a measure value of said conductivity to a corresponding value of osmolarity; and
   display means for displaying a visible representation of said value of osmolarity.

2. The osmometer of claim 1 wherein said probe means comprises a replaceable tip portion, a distal end of said tip portion having separated first and second electrically conductive electrodes and a gap associated therewith, and connection means for connecting, both mechanically and electrically, a proximal end of said tip portion to said conductivity measuring means.

3. The osmometer of claim 2 wherein proximal ends of said first and second electrodes are connected to corresponding mating fixtures of said connection means in said conductivity measuring means.

4. The osmometer of claim 2 further comprising separation means for keeping said first and second electrodes apart.

5. The osmometer of claim 4 wherein said first and second electrodes are kept a fixed distance apart by said separation means.

6. The osmometer of claim 2 further comprising nonconductive bridge means for spanning said gap.

7. The osmometer of claim 6 wherein said bridge means comprises a strip of absorbent material.

8. The osmometer of claim 7 wherein said absorbent material comprises paper.

9. The osmometer of claim 7 wherein said absorbent material comprises a thread of natural fibers.

10. The osmometer of claim 7 wherein said absorbent material comprises a thread of synthetic fibers.

11. The osmometer of claim 2 wherein said gap comprises an air gap between said first and second electrodes at said distal end.

12. The osmometer of claim 2 wherein each of said first and second electrodes has a distal end having a size suitable for contact with the human eye.

13. The osmometer of claim 12 wherein each of said first and second electrode distal ends comprises a gold surface.

14. The osmometer of claim 12 wherein each of said first and second electrode distal ends comprises a platinum surface.

15. The osmometer of claim 1 wherein said display means comprises a digital display.

16. The osmometer of claim 1 wherein said display means comprises an analog display.

17. An osmometer probe means adapted for contacting human eye tissue, and for making a conductivity measurement on, an in vivo sample of a bodily fluid on said human eye tissue, including: a conductive tip portion having a size adapted for safely contacting said bodily fluid on said human eye tissue, and conductivity-measuring means operatively connected to said conductive tip portion.

18. The osmometer probe means of claim 17 wherein said conductive tip portion includes a distal end, and a proximal end, and, at the distal end of said tip portion, first and second electrically-conductive electrodes and a gap associated with said electrodes, and means for connecting, mechanically and electrically, the proximal end of said tip portion to said conductivity measuring means.

* * * * *